(12) United States Patent
Bora et al.

(10) Patent No.: US 8,470,892 B2
(45) Date of Patent: Jun. 25, 2013

(54) METHOD OF INDUCING NEOVASCULARIZATION

(76) Inventors: Puran S. Bora, Little Rock, AR (US); Nalini S. Bora, Little Rock, AR (US)

( * ) Notice: Subject to any disclaimer, the term of this patent is extended or adjusted under 35 U.S.C. 154(b) by 336 days.

(21) Appl. No.: 12/806,336

(22) Filed: Aug. 10, 2010

(65) Prior Publication Data

US 2012/0041074 A1 Feb. 16, 2012

(51) Int. Cl.
*A61K 47/32* (2006.01)
*A61B 5/055* (2006.01)

(52) U.S. Cl. .................................. 514/772.4; 424/9.32

(58) Field of Classification Search .................. None
See application file for complete search history.

(56) References Cited

U.S. PATENT DOCUMENTS

2002/0013261 A1* 1/2002 Pawliuk et al. .................. 514/2

FOREIGN PATENT DOCUMENTS

WO WO/01/87312 11/2001

OTHER PUBLICATIONS

Mani et al., Enhancement of Wound Healing by Shikonin Analogue 93/637 in Normal and Impaired Healing, Skin Pharmacol Physiol 2004;17:49-56 (Abstract).*
Coleman, H.R., Chan, C.C, Ferris, L.F., Chew, E.Y., Age-related macular degeneration, Lancet, 2008, 1835-1845, vol. 372.
Visual impairment and blindness, World Health Organization Fact Sheet No. 282, May 2009.
Campochiaro, P.A., Retinal and choroidal neovascularization, Journal of Cellular Physiology, 2000, 301-310, vol. 184.
Gehrs, K.M., Anderson, D.H., Johnson, L.V., Hageman, G.S., Age-related macular degeneration-emerging pathogenic and therapeutic concepts, Annals of Medicine, 2006, 450-471, vol. 38.
Zarbin, M.A., Current Concepts in the Pathogenesis of Age-Related Macular Degeneration, Archives of Ophthalmology, 2004, 598-614, vol. 122.
Hamad, I., Hunter, A.C., Szebeni, J., Moghimi, S.M., Poly(ethylene glycol)s generate complement activiation products in human serum through increased alternative pathway turnover and a MASP-2-dependent process, Molecular Immunology, 2008, 225-232, vol. 46.
Arima, Y., Toda, M., Iwata, H., Complement activation on surfaces modified with ethylene glycol units, Biomaterials, 2008, 551-560, vol. 29.
Bora, P.S., Sohn, J.H., Cruz, J.M., Jha, P., Nishihori, H., Wang, Y., Kaliappan, S., Kaplan, H.J., Bora, N.S., Role of complement and complement membrane attack complex in laser-induced choroidal neovascularization, The Journal of Immunology, 2005, 491-497, vol. 174.
Jha, P., Bora, P.S., Nora, N.S., The role of complement system in ocular diseases including uveitiis and macular degeneration, Molecular Immunology, 2007, 3901-3908, vol. 44.
Nozaki, M., Raisler, B.J., Sakurai, E., Sarma, J.V., Barnum, S.R., Lambris, J.D., Chen, Y., Zhang, K., Ambati, B.K., Baffi, J.Z., Ambati, J., Drusen complement component C3a and C5a promote choroidal neovascularization, Proceedings of the National Academy of Sciences, 2006, 2328-2333, vol. 103.
Klein, R.J., Zeiss, C., Chew, E.Y., Tsai, J.Y., Sackler, R.S., Haynes, C., Henning, A.K., sanGiovanni, J.P., Mane, S.M., Mayne, S.T., Bracken, M.B., Ferris, F.L., Ott, J., Barnstable, C., Hoh, J., Complement factor H polymorphism in age-related macular degeneration, Science, 2005, 385-289, vol. 308.
Bora, N.S., Kaliappan, S., Jha, P., Xu, Q., Sivasankar, B., Harris, C.L., Morgan, B.P., Bora, P.S., CD59, a complement regulatory protein, controls choroidal neovascularization in a mouse model of wet-type age-related macular degeneration, The Journal of Immunology, 2007, 1783-1790, vol. 178.
Bora, P.S., Kaliappan, S., Xu, Q., Kumar, S., Wang, Y., Kaplan, H.J., Bora, N.S., Alcohol linked to enhanced angiogenesis in rat model of choroidal neovascularization, The FEBS Journal, 2006, 1403-1414, vol. 273.
Bora, N.S., Kaliappan, S., Jha, P., Xu, Q., Sohn, J.H., Dhaulakhandi, D.B., Kaplan, H.J., Bora, P.S., Complement activation via alternative pathway is critical in the development of laser-induced choroidal neovascularization: role of factor B and factor H., The Journal of Immunology, 2006, 1872-1878, vol. 177.
Ambati, J., Anand, A., Fernandez, S., Sakurai, E., Lynn, B.C., Kuziel, W.A., Rollins, B.J., Ambati, B.K., An animal model of age-related macular degeneration in senescent Ccl-2- or Ccr-2-deficient mice, Nature Medicine, 2003, 1390-1397, vol. 9.
Montezuma, S.R., Vavvas, D., Miller, J.W., Review of the ocular angiogenesis animal models, Seminars in Opthalmology, 2009, 52-61, vol. 24.
Rakoczy, P.E., Yu, M.J., Nusinovvitz, S., Chang, B., Heckenlively, J.R., Mouse models of age-related macular degeneration, Experimental Eye Research, 2006, 741-752, vol. 82.
Ryan, S.J., The development of an experimental model of subretinal neovascularization in disciform macular degeneration, Transactions of the American Opthalmological Society, 1979, 707-745, vol. 77.
Ishibashi, T., Miller, H., Orr, G., Sorgente, N., Ryan, S.J., Morphologic observations on experimental subretinal neovascularization in the monkey, Investigative Opthalmology & Visual Science, 1987, 1116-1130, vol. 28.
Kimura, H., Sakamoto, T., Hinton, D.R., Spee, C., Ogura, Y., Tabata, Y., Ikada, Y., Ryan, S.J., A new model of subretinal neovascularization in the rabbit, Investigative Opthalmology & Visual Science, 1995, 2110-2119, vol. 36.
Cui, J.Z., Kimura, H., Spee, C., Thumann, G., Hinton, D.R., Ryan, S.J., Natural history of choroidal neovascularization induced by vascular endothelial growth factor in the primate, Graefes Archive for Clinical and Experimental Ophthalmology, 2000, 326-333, vol. 238.
Edwards, A.O., Malek, G., Molecular genetics of AMD and current animal models, Angiogenesis, 2007, 119-132, vol. 10.

(Continued)

*Primary Examiner* — Sreeni Padmanabhan
*Assistant Examiner* — Svetlana M Ivanova
(74) *Attorney, Agent, or Firm* — Richard Blakely Glasgow (57) ABSTRACT

A method for inducing neovascularization in which a pharmaceutically effective amount of polyethylene glycol (PEG) is injected into the tissue of the subject for purposes of accelerating wound healing and mimicking age related macular degeneration, cancer, tumors, and atherosclerosis for further research purposes.

3 Claims, 8 Drawing Sheets
(7 of 8 Drawing Sheet(s) Filed in Color)

OTHER PUBLICATIONS

Miller, H., Miller, B., Ishibashi, T., Ryan, S.J., Pathogenesis of laser-induced choroidal subretinal neovascularization, Investigative Ophthalmology & Visual Science, 1990, 899-908, vol. 31.

Zhu, Z.R., Goodnight, R., Sorgente, N., Ogden, T.E., Ryan, S.J., Experimental subretinal neovascularization in the rabbit, Archives of Ophthalmology, 1988, 406-411, vol. 106.

Luhmann, U.F., Robbie, S., Munro, P.M., Barker, S.E., Duran, Y., Luong, V., Fitzke, F.W., Bainbridge, J.W., Ali, R.R., MacLAREN, R.E., The drusenlike phenotype in aging Ccl-2-knockout mice is caused by an accelerated accumulation of swollen autofluorescent subretinal macrophages, Investigative Ophthalmology & Visual Science, 2009, 5934-5943, vol. 50.

Imamura, Y, Noda, S., Hashizume, K, Shinoda, K., Yamaguchi, M., Uchiyama, S., Shimizu, T., Mizushima, Y., Shirasawa, T., Tsubota, K., Drusen, chorodial neovascularization, and retinal pigment epithelium dysfunction in SOD1-deficient mice: a model of age-related macular degeneration, Proceedings of the National Academy of Sciences, 2006, 11282-11287, vol. 103.

Malek, G., Johnson, L.V., Mace, B.E., Saloupis, P., Schmechel, D.E., Rickman, D.W., Toth, C.A., Sullivan, P.M., Rickam, C.B., Apoliprotein E allele-dependent pathogenesis: a model for age-related retinal degeneration, Proceedings of the National Academy of Sciences, 2005, 11900-11905, vol. 102.

Shen, W.Y., Rakoczy, P.E., Uptake dynamics and retinal tolerance of phosphorothioate oligonucleotide and its direct delivery into the site of choroidal neovascularization through subretinal administration in the rat, Antisense and Nucleic Acid Drug Development, 2001, 257-264, vol. 11.

Zhu, Z-R., Goodnight, R., Sorgente, N., Ogden, T.E., Ryan, S.J., Experimental subretinal neovascularization in the rabbit, Graefe's Archive of Ophthalmology, 1989, 257-262, vol. 227.

Anderson, D.H., Radeke, M.J., Gallo, N.B., Chapin, E.A., Johnson, P.T., Curletti, C.R., Hancox, L.S., Hu, J., Ebright, J.N., Malek, G., Hauser, M.A., Rickman, C.B., Bok, D., Hageman, G.S., Johnson, L.V., The pivotal role of the complement system in aging and age-related macular degeneration: Hypothesis revisited, Progress in Retinal and Eye Research, 2010, 95-112, vol. 29.

Hsu, H T. Goodnight, R., Ryan, S.J., Subretinal choroidal neovascularization as a response to penetrating retinal injury in the pigmented rabbit, Japanese Journal of Ophthalmology, 1989, 358-366, vol. 33.

Ishida, T., Kazutaka, A., Wang, X.Y., Kiwada, H., Accelerated blood clearance of PEGylated liposomes upon repeated injections: Effect of doxorubicin-encapsulation and high-dose first injection, Journal of Controlled Release, 2006, 251-258, vol. 115.

* cited by examiner

METHOD OF INDUCING NEOVASCULARIZATION

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

1. Field of the Invention

The present invention relates generally to a method for inducing neovascularization and, in particular, to a method of inducing neovascularization mimicking age related macular degeneration, cancer, tumors, atherosclerosis, and wound healing for purposes of further research.

2. Brief Description of the Related Art

Neovascularization or angiogenesis is the formation of new blood vessels from existing vessels. Neovascularization aids in the natural process of wound healing. By increasing the rate of neovascularization, the rate of wound healing is also accelerated. Neovascularization is also the hallmark of the development of macular degeneration, tumors, cancer, and atherosclerosis. However, a method of inducing neovascularization can be a valuable tool in further research investigations of these conditions.

Macular degeneration is a clinical term that is used to describe a family of diseases that are characterized by a progressive loss of central vision associated with abnormalities of the choroid, the neural retina and/or the retinal pigment epithelium (RPE). Under the retina is the choroid, a collection of blood vessels embedded within fibrous (connective) tissue, and the pigmented epithelium, which overlays the choroid layer. The choroidal blood vessels provide nutrition to the retina. The RPE cells produce, store, and transport a variety of factors that are responsible for the normal function and survival of photoreceptors [1].

Age-related macular degeneration (AMD), the most prevalent macular degeneration, is associated with progressive loss of visual activity in the central portion of the visual field, changes in color vision, and abnormal dark adaptation and sensitivity. Two principal clinical manifestations of AMD have been described as the dry, or atrophic, form, and the wet, or exudative, form [1-4].

Wet AMD is caused by choroidal neovascularization (CNV) and vascular leakage, resulting in displacement of the retina, hemorrhage and scar formation. As the blood vessels leak fluid and blood, scar tissue is formed that destroys the central retina. Wet AMD with choroidal neovascularization leads to reduction of vision and blindness in 75% of cases [5]. There are no current methods of prevention or cure of AMD and only palliative treatment is available.

AMD has numerous causative factors and a complex pathogenesis. However, induction of CNV is known to be a critical event in the progression of the disease. Polyethylene glycol (PEG) is a newly discovered activator of the complement system [7-8]. It was recently discovered that activation of the complement system plays a key role in the development of CNV [9-17]. Animal models mimicking the pathological processes during wet AMD are limited to laser induced CNV. Very limited animal models reproduce CNV: laser treatment, surgical debridement of the RPE cells and mechanical rupture of Bruch's membrane, increased expression of growth factors or use of transgenic animals [18-26].

The laser induced models require expensive laser machinery and microscopes. The laser model also causes substantial damage to other portions of the eye, including the retina. CNV was detected in rabbits after penetrating retinal injury [27]. As in the case of laser induced CNV, RPE cells, Bruch's membrane and choroid damage resulted [27]. Subretinal injection models have been utilized to induce CNV, but these models are limited in their applicability. Specifically, CNV was induced in rabbits after subretinal injection of vitreous without rupture of Bruch's membrane, but it was a technically complex method of vitreous aspiration and this model is not applicable on mice because of extremely low amount of vitreous in mouse eye [28, 29]. In addition, models with subretinal injection of bFGF microspheres [23] or [VEGF]-impregnated microspheres [24] requires at least these microspheres and does not reflect completely pathogenesis of AMD with involvement of complement system. Transgenic mice models for inducing have also be used with variable results. CNV in CCL2-/- mice was noted [18] but not confirmed by others [30]. CNV in SOD1-/-mice was detected only in some animals [31]. Apolipoprotein E4 transgenic mice showed signs of CNV in approximately in 20% of cases in second year of life [32].

It would therefore be desirable to develop a method for inducing neovascularization mimicking age related macular degeneration, cancer, tumors, and atherosclerosis in a short period of time that does not require expensive equipment and minimizes collateral damage to the subject. It would also be desirable to develop a method for inducing neovascularization to accelerate wound healing. The limitations of the prior art are overcome by the present invention as described below.

BRIEF SUMMARY OF THE INVENTION

The present invention relates to a method of inducing neovascularization. The method of the present invention comprises locally injecting into a subject a pharmaceutically effective amount of PEG.

While the present invention is described with specific reference to AMD, the method of inducing neovascularization of the present invention is not so limited and may be employed in the treatment of other conditions, such as cancer, tumors, and atherosclerosis. It may also be utilized in wound healing.

It is therefore an object of the present invention to provide for a method for inducing neovascularization that is quicker, cheaper, and minimizes the collateral damage to the subject as compared to the prior art.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

With reference to FIGS. 1-8B, the preferred embodiment of the present invention may be described.

EXAMPLES

Male C57BL/6 mice (7-9 weeks old) were anesthetized with Ketamine (80 mg/kg) and Xylazine (20 mg/kg) prior to subretinal injection. One eye was decompressed with 27G needle by inserting the needle through the limbus and sclera. Microinjector UMP3 equipped with Nanofil syringe 100 µL and 33G blunt needle (Word Precision Instruments) was used for injections. The needle was inserted into the incision created by decompression. Movement of the needle was stopped when light resistance was felt by operator. Solutions (single injection of 2 µL) were injected slowly for 5 seconds in the subretinal space. All manipulations were performed under visual control using microscope. Detachment of the retina was visible through the lens. The second eyes of mice were not injected.

To investigate dose dependent effect of PEG-8 (Polyethylene glycol 400) the inventors divided the animals into 7 groups: one control group (n=3 mice) which was not treated at all, group 2 (n=3 mice) received a single subretinal injection of vehicle (2 µL of 0.9% sterile sodium chloride), and five experimental groups which were injected with different doses of PEG-8: 2.0 mg, 1.0 mg, 0.5 mg, 0.25 mg and 0.125 mg. PEG-8 was dissolved in vehicle before injection. Doses of PEG-8 were delivered to the one experimental eye in 2 µL respectively. To determine optimal dose of PEG-8, the inventors performed histological examination and investigation of flat mounted RPE-choroid-sclera complexes after perfusion of animals with FITC-dextran solution at day 14 after injection.

Figure 1:
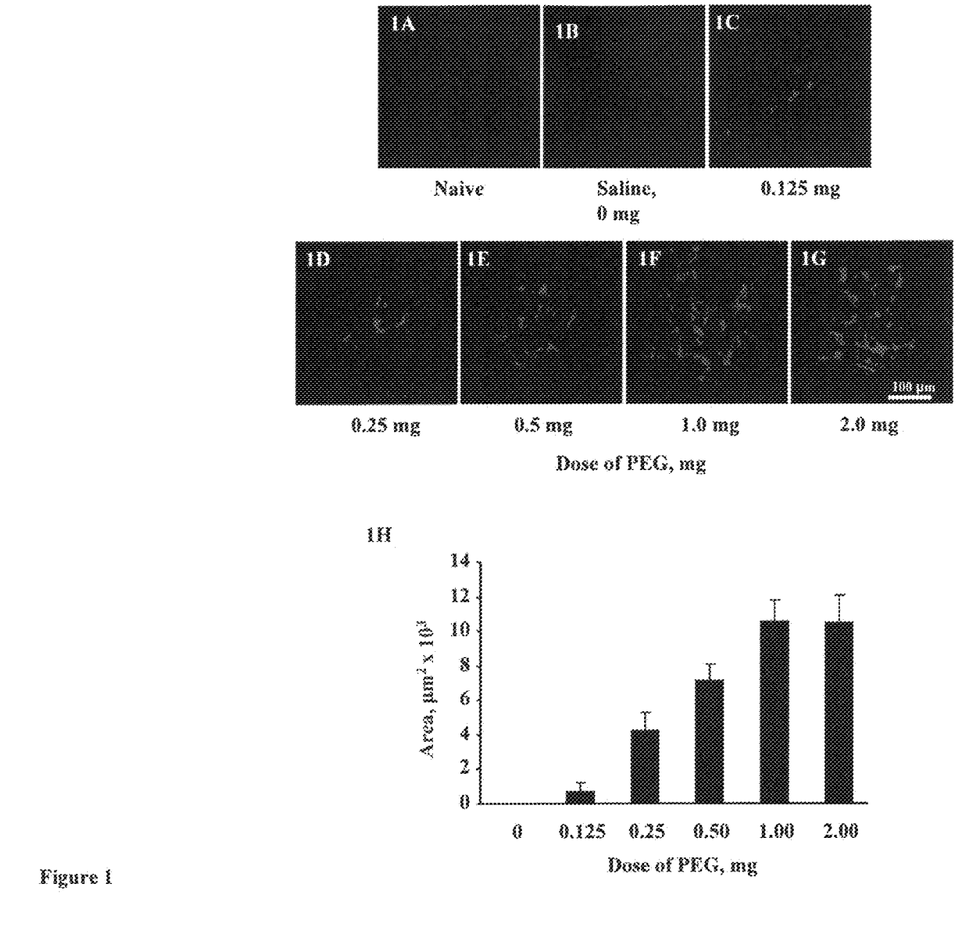
FIGS. 1A-G are confocal micrographs illustrating CNV (green color) after injection of different doses of PEG-8.
FIG. 1H is a graph showing the effect of different amounts of PEG on CNV size.

The mice were sacrificed at day 14 after subretinal injection of PEG-8. As shown in Table 1, the inventors found CNV in all investigated groups. The 1.0 mg dose induced CNV of the largest size and frequency (4.4 sites of CNV per eye) (FIG. 1).

Figure 2:
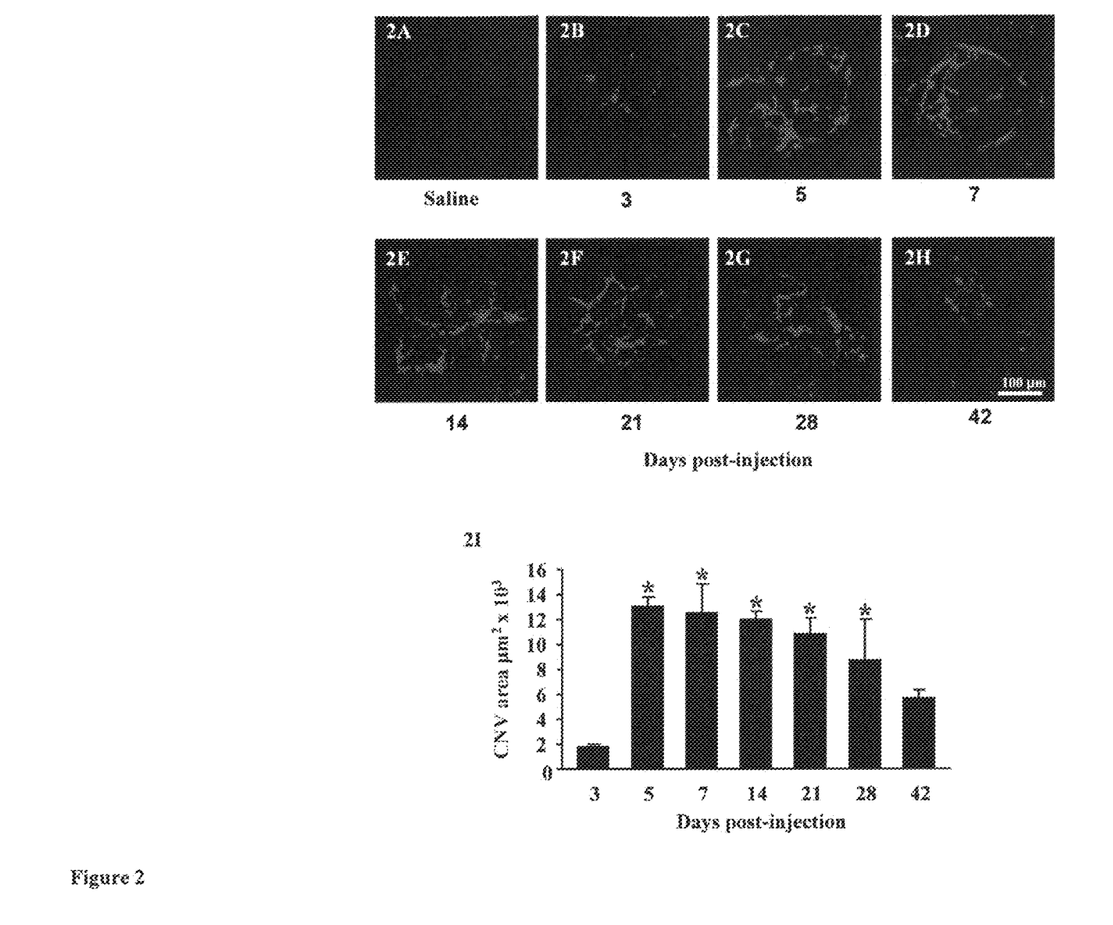
FIGS. 2A-H are confocal micrographs illustrating CNV (green color) after periods of time after injection.
FIG. 2I is a graph showing the effect of time after injection on CNV size.
Figure 3:
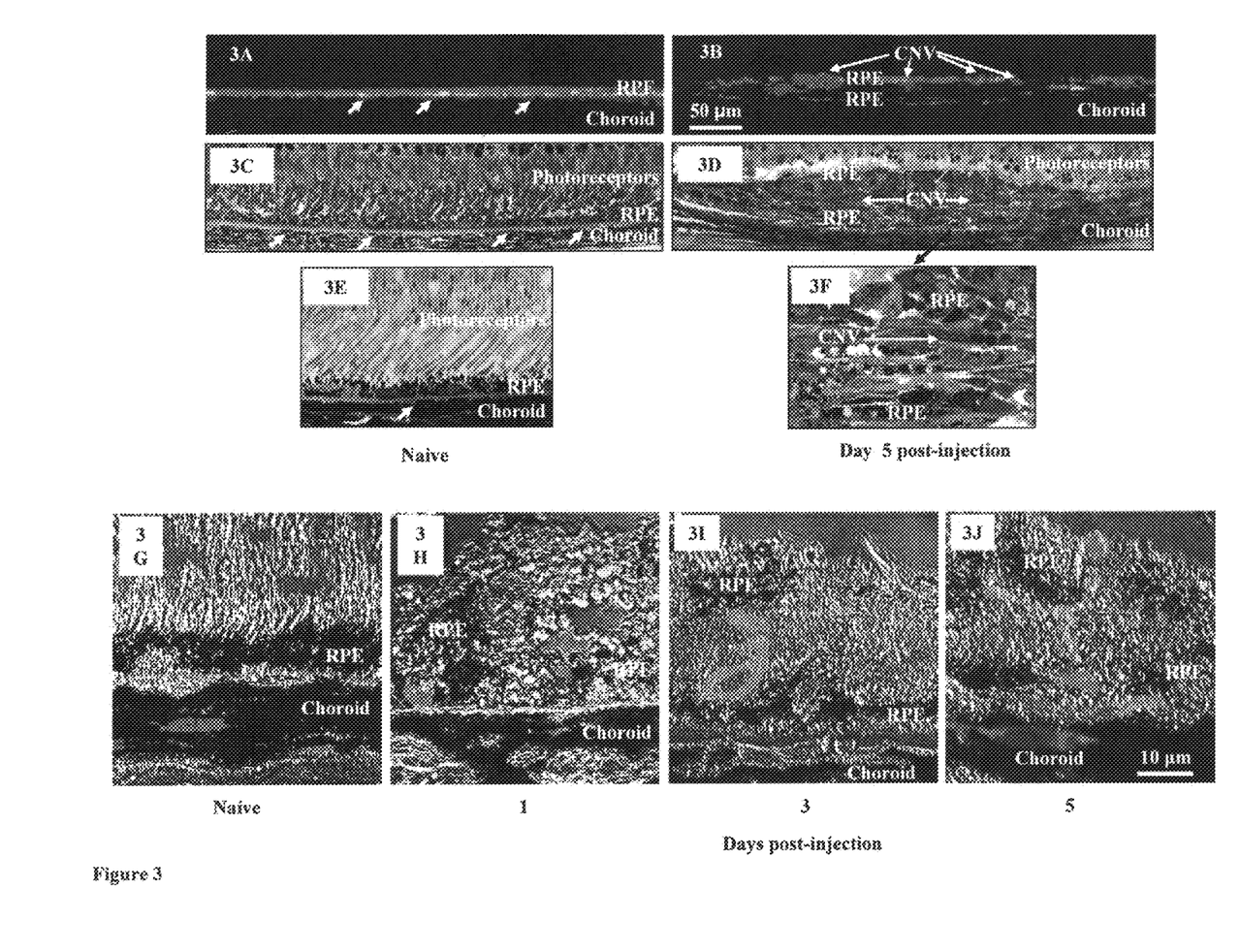
FIGS. 3A-B are saggital views of 3D reconstruction of RPE-choroid flat mounts of normal and PEG-8 treated animals (FITC-dextran perfused vessels are green and RPE cells are red).
FIGS. 3C-F are microphotographs of semithin (1 µm) upon embedded eye sections of normal and PEG-8 injected mice.
FIGS. 3G-J are micrographs of paraffin eye sections of normal and PEG-8 injected mice.
Figure 4:
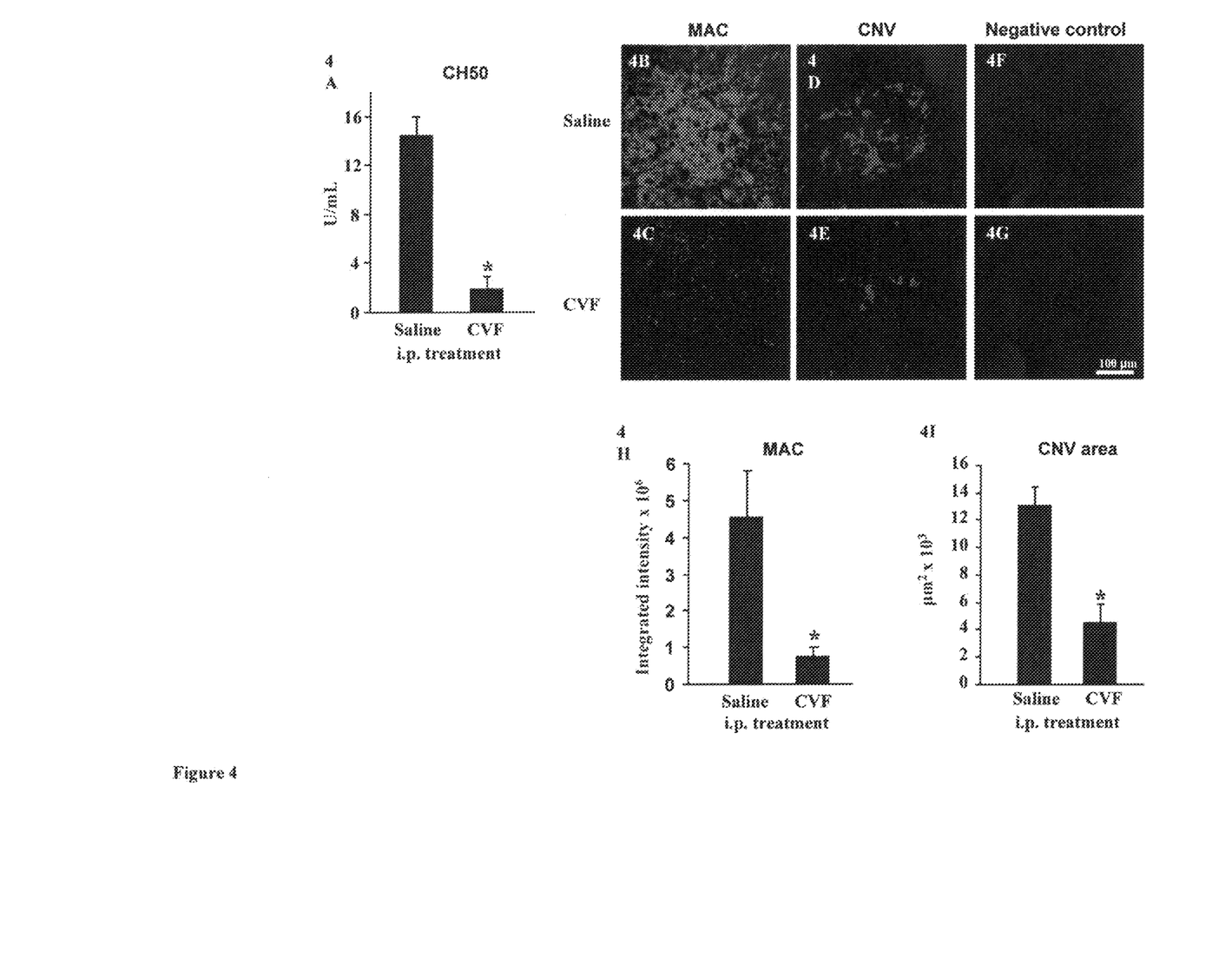
FIG. 4A is a graph showing the effect of complement depletion with Cobra Venom Factor (CVF) in mouse serum.
FIGS. 4B-C are micrographs illustrating the MAC deposition after depletion of the complement system.
FIGS. 4D-E are micrographs illustrating CNV size after depletion of the complement system.
FIGS. 4F-G are micrographs of the control.
FIG. 4H is a graph showing the effect of complement depletion on MAC deposition.
FIG. 4I is a graph showing the effect of complement depletion on the size of CNV.
Figure 5:
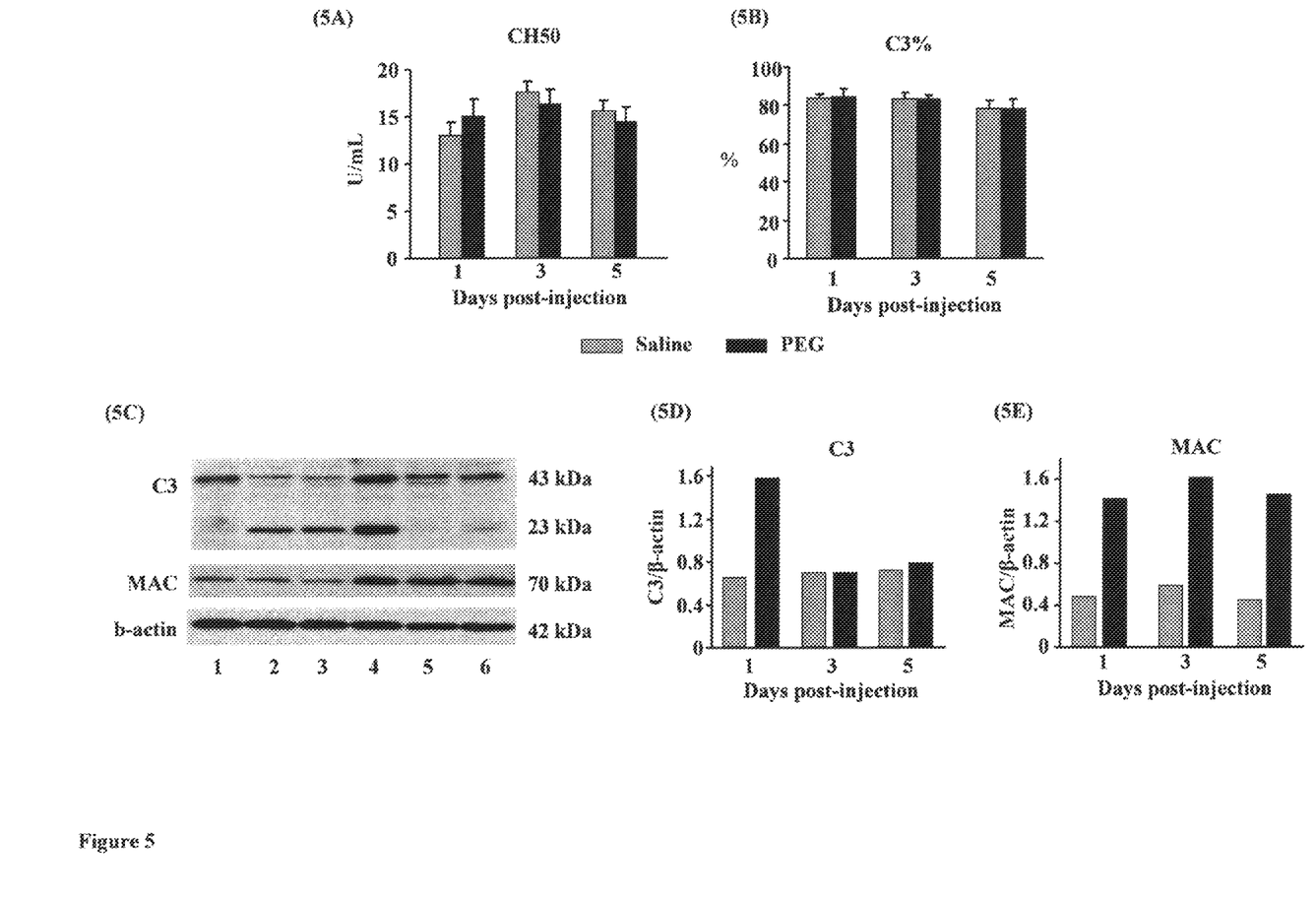
FIG. 5A is a graph showing the effect of PEG on total complement activity in mouse serum.
FIG. 5B is a graph showing the effect on PEG on complement activation by alternative pathway in mouse serum.
FIG. 5C is a western blot analysis of RPE-choroid tissue.
FIG. 5D is a graph showing the effect of PEG on C3 split products.
FIG. 5E is a graph showing the effect of PEG on MAC.

To investigate the time course of CNV after PEG-injection, the animals were injected with 1.0 mg of PEG-8 subretinally and 5 mice from each group were sacrificed at day 1, 3, 5, 7, 14, 21, 28, and 42 post-injection. As shown in FIG. 2, first signs of CNV were detected as early as day 3 after treatment. CNV reached maximal size at day 5 and was present until at least day 42.

To evaluate the CNV size, the animals were perfused through their heart with 0.75 ml of phosphate-buffered saline (PBS) containing 50 mg/ml of fluorescein-labeled dextran (FITC-Dextran, 2 million average mw) before they were sacrificed. The eyes were harvested and fixed for 4 hours in 10% phosphate buffered formalin and RPE-choroid-sclera flat mounts were prepared. The RPE-choroid-sclera complexes were mounted in ProLong Antifade reagent with the sclera facing down and were examined under a ZEISS LSM 510 laser confocal microscope.

Confocal microscopy of flat mounted RPE-choroids perfused with FITC-dextran was performed and investigated with semi thin (1 µm) embedded sections at day 5 after injection when CNV was fully developed. Analysis of flat mounts and semi thin sections showed that in naive mice RPE formed single layer of cells (FIGS. 3A, C, E) and vessels were located exclusively within choroid (FIGS. 3A, C, E). After PEG-8 injection, CNV was located between two layers of RPE cells in subretinal space (FIGS. 3B, D, F). No vessels originated from retina was found (FIG. 3D). 5 µm paraffin section of control (saline) and PEG-8 injected mice at day 1 were investigated, 3 and 5 after treatment. RPE cells in control groups formed single layer of cells and endothelial cells were found within choroid (FIG. 3G). Starting from day 1 after PEG-8 treatment, zones of affected RPE cell structure were discovered with increased size, irregular shape and presence of space between neighboring RPE cells (FIG. 3H). Isolectin-IB4 positively labeled cells located between affected RPE cells were found at day 1, 3 and 5 after injection (FIGS. 3H-J). Isolectin-IB4 positive had contact with choroidal Isolectin-IB4 positive capillaries and formed vessels in subretinal tissue between existing and newly formed RPE cell layers (FIG. 3J).

To investigate dependence of PEG-8 induced CNV on complement system activation, the complement system in the mice was depleted by intraperitoneal administration of Cobra Venom Factor. Four groups of animals were used (n=5 mice in each group). Group 1 and 2 were treated intraperitoneal with 4 U of cobra venom factor as described in the inventors' previous publication [11] for 2 days before and every day after subretinal injections. Group 3 and 4 were injected intraperitoneal with vehicle (0.9% Sodium Chloride).

The mice were then injected with subretinal PEG-8 and investigated at day 5 after treatment. Total complement activity in serum of CVF treated mice was significantly reduced compared to saline injected animals (p<0.05, FIG. 4A). RPE-choroids of these mice were stained for MAC by IHC and investigated flat mounts using confocal microscopy. Areas of high MAC deposition in animals treated with saline (FIG. 4B) were found but not in CVF treated group (FIG. 4C). MAC positive fluorescence in saline treated animals was significantly higher compared to CVF injected mice (FIG. 4H, $p<0.05$). Analysis of CNV size showed that treatment with CVF significantly (3 fold, $p<0.05$, FIG. 4I) reduced area of FITC-dextran perfused vessels.

Activation of the complement system by PEG-8 was also studied in the RPE-choroid and in the blood. PEG-8 or saline was injected subretinally and animals were sacrificed at day 1, 3 and 5 after treatment. Total complement activation was studied in the serum. Levels of C3 split products and MAC were investigated in RPE-choroid tissue. PEG-8 did not affect total and alternative complement activity in mouse serum at all investigated time points (FIG. 5A, B). A three-fold increase of C3 split products levels in PEG-8 injected animals compared to saline injected mice was observed only at day 1 post-injection (FIGS. 5C, D). PEG-8 and saline injected animals at day 3 and 5 had the same levels of total C3 (43 kDa and 23 kDA), but levels of C3 (43 kDa) were higher in PEG-8 treated animals compared to saline injected mice (FIGS. 5C, D). Western blotting showed that in PEG-8 treated mice MAC levels were approximately three fold higher compared to saline treated animals at all investigated time points (FIGS. 5C, E).

Figure 6:
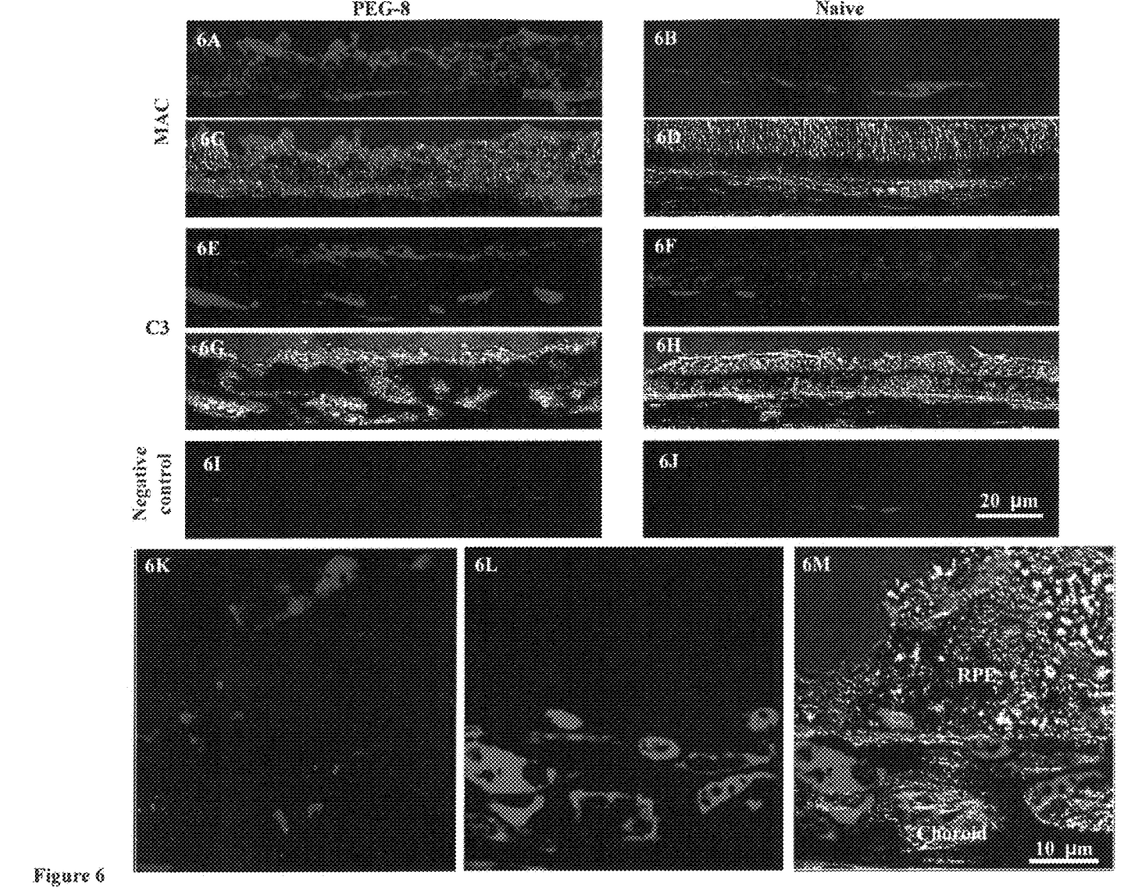
FIGS. 6A-M are micrographs with immunohistochemical staining for C3 and MAC in site of CNV induction (green color).
Figure 7:
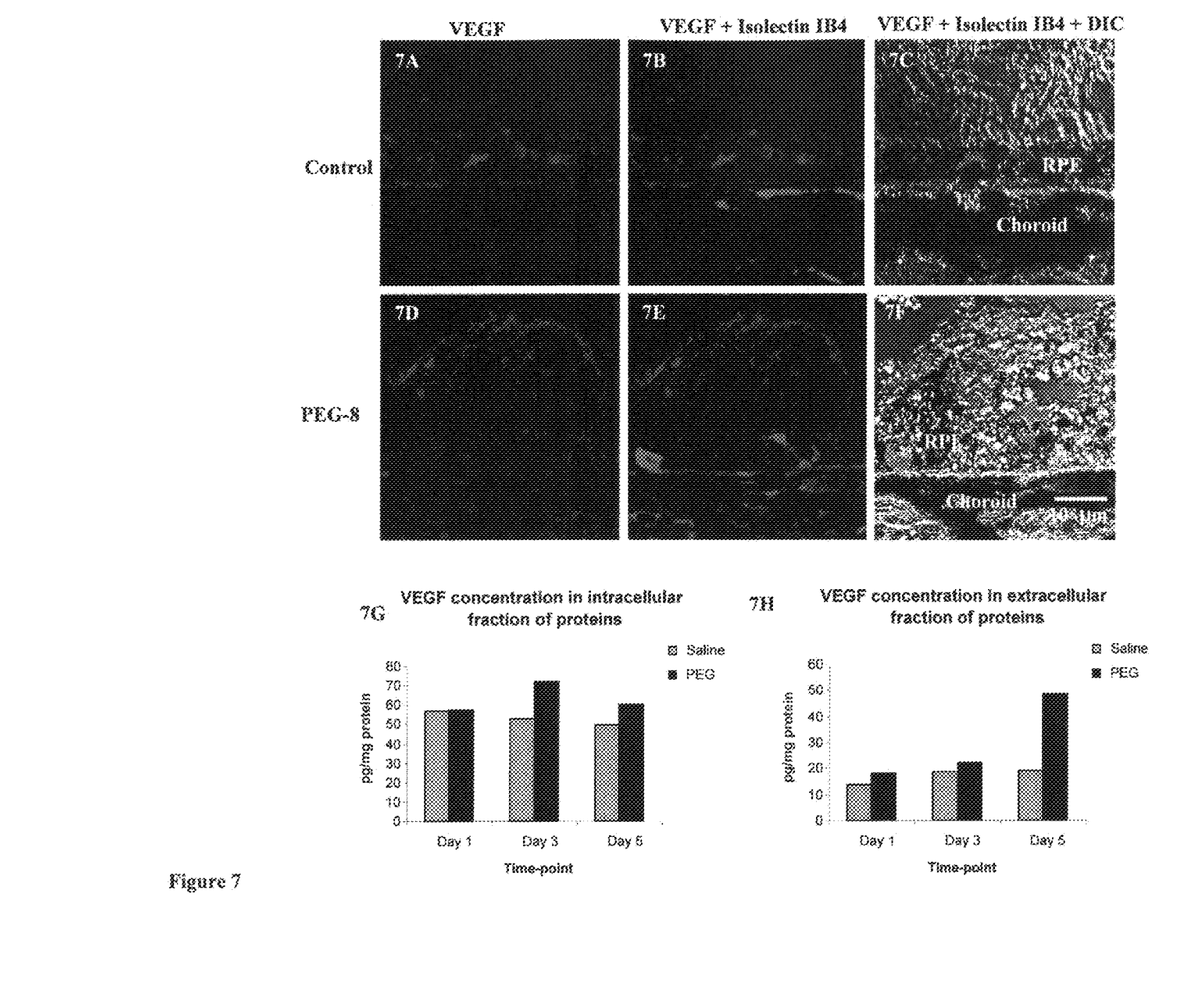
FIGS. 7A-F are micrographs illustrating the effect of PEG on localization and amount of VEGF in RPE-choroid.
FIGS. 7G-H are graphs showing the effect of time on the VEGF concentration in RPE-choroid.
Figure 8:
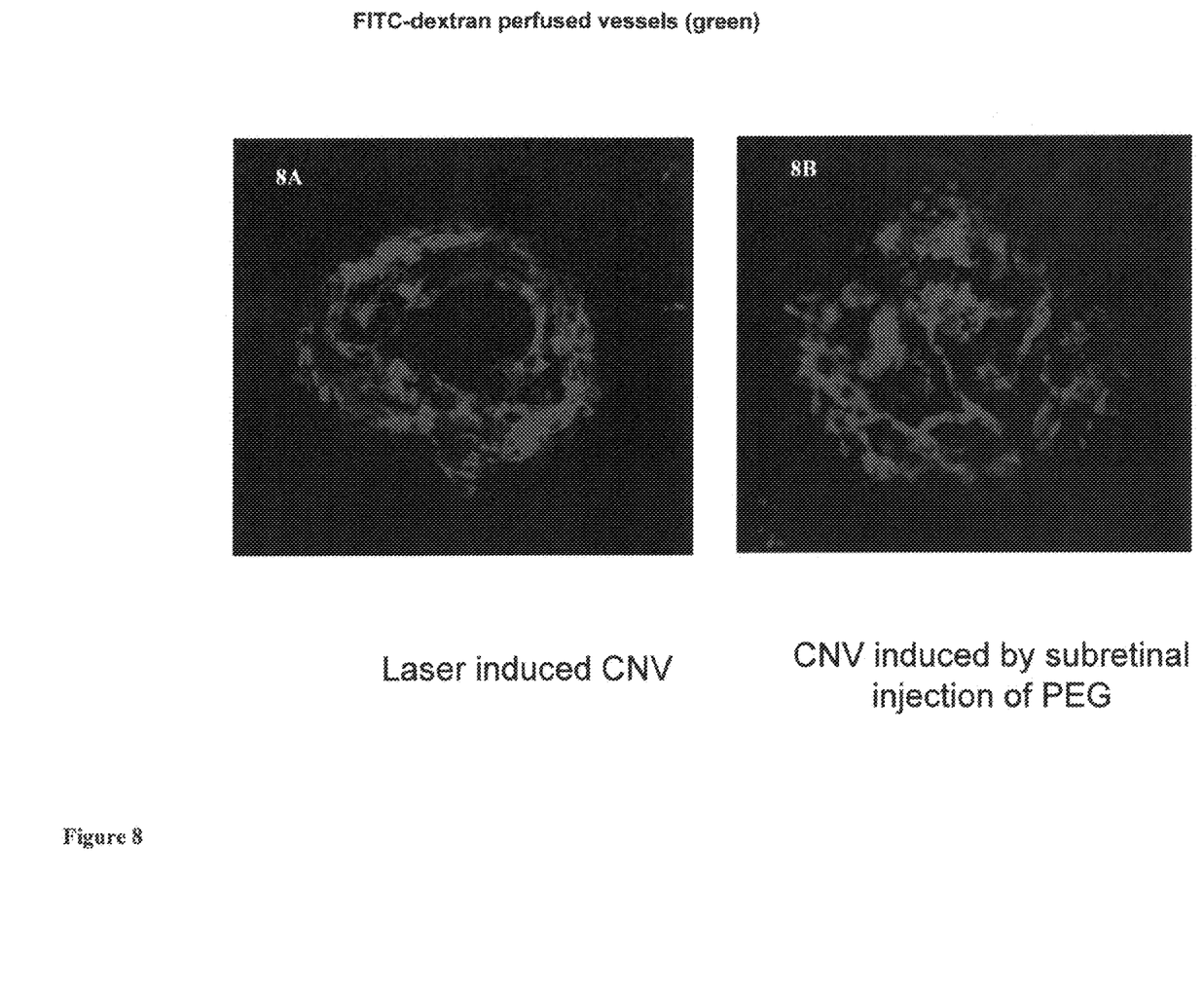
FIGS. 8A-B are micrographs showing the difference between CNV formation using laser induced methodology and PEG-induced methodology (green color).

An IHC colocalization experiment was performed to find the relationship between C3/MAC deposition, VEGF secretion and initiation of CNV growth. MAC was found mostly in sites of C3 deposition (FIG. 6). It was discovered that CNV growth took place in sites of extremely high deposition of C3 and MAC on the surface of RPE cells and in choroid (FIG. 6). At the same locations, release of VEGF from RPE cells and distribution of this growth factor within Bruch's membrane and choroid was observed (FIG. 7). Choroidal capillaries were colocalized with VEGF (FIG. 7). ELISA analysis of VEGF levels showed increase of VEGF in intra- and extracellular fraction of proteins obtained from posterior part of the eyes (FIGS. 7G, H). Comparison of new vessel growth is shown in FIGS. 8A-B; laser induced model (A) and PEG-induced model (B) CNV. Green color shows the size of new vessel growth in both the figures.

Damage of RPE-choroid after subretinal injection is much smaller compared to laser treatment or surgical procedures. Local (intraocular) stimulation of VEGF expression and secretion by PEG-8 mimic changes in human AMD.

For purposes of mimicking cancer, tumor formation, atherosclerosis, and aiding in wound healing, PEG can be locally injected into the tissue or, if applicable, applied directly to the tissue in the form of a gel or ointment.

REFERENCES

1. Coleman H R, Chan C C, Ferris 3rd F L, Chew E Y: Age-related macular degeneration. Lancet 2008, 372: 1835-1845
2. Visual impairment and blindness, Word Health Organization, Fact Sheet No 282, May 2009.
3. Campochiaro P A: Retinal and choroidal neovascularization. J Cell Physiol 2000, 184:301-310.
4. Gehrs K M, Anderson D H, Johnson L V, Hageman G S: Age-related macular degeneration-emerging pathogenetic and therapeutic concepts. Ann Med 2006, 38:450-471.
5. Zarbin M A. Current concepts in the pathogenesis of age-related macular degeneration. Arch Ophthalmol. 2004 April; 122(4):598-614.
6. Hamad I, Hunter A C, Szebeni J, Moghimi S M. Poly(ethylene glycol)s generate complement activation products in human serum through increased alternative pathway turnover and a MASP-2-dependent process. Mol Immunol. 2008 December; 46(2):225-32. Epub 2008 Oct. 11.
7. Arima Y, Toda M, Iwata H. Complement activation on surfaces modified with ethylene glycol units. Biomaterials. 2008 February; 29(5):551-60. Epub 2007 Nov. 5.
8. Ishida T, Atobe K, Wang X, Kiwada H. Accelerated blood clearance of PEGylated liposomes upon repeated injections: effect of doxorubicin-encapsulation and high-dose first injection. J Control Release. 2006 Oct. 27; 115(3): 251-8. Epub 2006 Sep. 3.
9. Anderson D H, Radeke M J, Gallo N B, Chapin E A, Johnson P T, Curletti C R, Hancox L S, Hu J, Ebright J N, Malek G, Hauser M A, Rickman C B, Bok D, Hageman G S, Johnson L V. The pivotal role of the complement system in aging and age-related macular degeneration: hypothesis re-visited. Prog Retin Eye Res. 2010 March; 29(2):95-112.
10. Bora P S, Sohn J H, Cruz J M, Jha P, Nishihori H, Wang Y, Kaliappan S, Kaplan H J, Bora N S. Role of complement and complement membrane attack complex in laser-induced choroidal neovascularization. J. Immunol. 2005 Jan. 1; 174(1):491-7.
11. Bora P S, Sohn J H, Cruz J M, Jha P, Nishihori H, Wang Y, Kaliappan S, Kaplan H J, Bora N S: Role of complement and complement membrane attack complex in laser-induced choroidal neovascularization. J Immunol 2005, 174: 491-497.
12. Jha P, Bora P S, Bora N S: The role of complement system in ocular diseases including uveitis and macular degeneration. Mol Immunol 2007, 44:3901-3908.
13. Nozaki M, Raisier B J, Sakurai E, Sarma J V, Barnum S R, Lambris J D, Chen Y, Zhang K, Ambati B K, Baffi J Z, Ambati J: Drusen complement component C3a and C5a promote choroidal neovascularization. Proc Natl Acad Sci USA 2006, 103:2328-2333
14. Klein R J, Zeiss C, Chew E Y, Tsai J Y, Sackler R S, Haynes C, Henning A K, sanGiovanni J P, Mane S M, Mayne S T, Bracken M B, Ferris F L, Ott J, Barnstable C, Hoh J: Complement factor H polymorphism in age-related macular degeneration. Science 2005, 308:385-389.
15. Bora N S, Kaliappan S, Jha P, Xu Q, Sivasankar B, Harris C L, Morgan B P, Bora P S: CD59, a complement regulatory protein, controls choroidal neovascularization in a mouse model of wet-type age-related macular degeneration. J Immunol 2007, 178:1783-1790.
16. Bora P S, Kaliappan S, Xu Q, Kumar S, Wang Y, Kaplan H J, Bora N S. Alcohol linked to enhanced angiogenesis in rat model of choroidal neovascularization. FEBS J. 2006 April; 273(7):1403-14.
17. Bora N S, Kaliappan S, Jha P, Xu Q, Sohn J H, Dhaulakhandi D B, Kaplan H J, Bora P S. Complement activation via alternative pathway is critical in the development of laser-induced choroidal neovascularization: role of factor B and factor H. J. Immunol. 2006 Aug. 1; 177(3):1872-8.
18. Ambati J, Anand A, Fernandez S, Sakurai E, Lynn B C, Kuziel W A, Rollins B J, Ambati B K. An animal model of age-related macular degeneration in senescent Ccl-2- or Ccr-2-deficient mice. Nat Med. 2003 November; 9(11): 1390-7.
19. Montezuma S R, Vavvas D, Miller J W. Review of the ocular angiogenesis animal models. Semin Ophthalmol. 2009 March-April; 24(2):52-61.
20. Elizabeth Rakoczy P, Yu M J, Nusinowitz S, Chang B, Heckenlively J R. Mouse models of age-related macular degeneration. Exp Eye Res. 2006 May; 82(5):741-52.

21. Ryan S J. The development of an experimental model of subretinal neovascularization in disciform macular degeneration. Trans Am Ophthalmol Soc. 1979; 77:707-45.
22. Ishibashi T, Miller H, Orr G, Sorgente N, Ryan S J. Morphologic observations on experimental subretinal neovascularization in the monkey. Invest Ophthalmol Vis Sci. 1987 July; 28(7):1116-30.
23. Kimura H, Sakamoto T, Hinton D R, Spee C, Ogura Y, Tabata Y, Ikada Y, Ryan S J. A new model of subretinal neovascularization in the rabbit. Invest Ophthalmol Vis Sci. 1995 September; 36(10):2110-9.
24. Cui J Z, Kimura H, Spee C, Thumann G, Hinton D R, Ryan S J. Natural history of choroidal neovascularization induced by vascular endothelial growth factor in the primate. Graefes Arch Clin Exp Ophthalmol. 2000 April; 238(4):326-33.
25. Edwards A O, Malek G. Molecular genetics of AMD and current animal models. Angiogenesis. 2007; 10(2):119-32.
26. Miller H, Miller B, Ishibashi T, Ryan S J. Pathogenesis of laser-induced choroidal subretinal neovascularization. Invest Ophthalmol Vis Sci. 1990 May; 31(5):899-908.
27. Hsu H T, Goodnight R, Ryan S J. Subretinal choroidal neovascularization as a response to penetrating retinal injury in the pigmented rabbit. Jpn J. Ophthalmol. 1989; 33(3):358-66.
28. Zhu Z R, Goodnight R, Sorgente N, Ogden T E, Ryan S J. Experimental subretinal neovascularization in the rabbit. Graefes Arch Clin Exp Ophthalmol. 1989; 227(3):257-62.
29. Zhu Z R, Goodnight R, Sorgente N, Blanks J C, Ogden T E, Ryan S J. Cellular proliferation induced by subretinal injection of vitreous in the rabbit. Arch Ophthalmol. 1988 March; 106(3):406-11.
30. Luhmann U F, Robbie S, Munro P M, Barker S E, Duran Y, Luong V, Fitzke F W, Bainbridge J W, Ali R R, MacLaren R E. The drusenlike phenotype in aging Ccl2-knockout mice is caused by an accelerated accumulation of swollen autofluorescent subretinal macrophages. Invest Ophthalmol Vis Sci. 2009 December; 50(12):5934-43.
31. Imamura Y, Noda S, Hashizume K, Shinoda K, Yamaguchi M, Uchiyama S, Shimizu T, Mizushima Y, Shirasawa T, Tsubota K. Drusen, choroidal neovascularization, and retinal pigment epithelium dysfunction in SOD1-deficient mice: a model of age-related macular degeneration. Proc Natl Acad Sci USA. 2006 Jul. 25; 103(30):11282-7.
32. Malek G, Johnson L V, Mace B E, Saloupis P, Schmechel D E, Rickman D W, Toth C A, Sullivan P M, Bowes Rickman C. Apolipoprotein E allele-dependent pathogenesis: a model for age-related retinal degeneration. Proc Natl Acad Sci USA. 2005 Aug. 16; 102(33):11900-5.
33. Shen W Y, Rakoczy P E. Uptake dynamics and retinal tolerance of phosphorothioate oligonucleotide and its direct delivery into the site of choroidal neovascularization through subretinal administration in the rat. Antisense Nucleic Acid Drug Dev. 2001 August; 11(4):257-64.

What is claimed is:

1. A method of mimicking age-related macular degeneration in a research subject comprising locally injecting a chemical into an eye of said subject in an amount effective to induce choroidal neovascularization, wherein said chemical consists essentially of polyethylene glycol.

2. The method of claim 1, wherein said amount effective to induce choroidal neovascularization is in the range of 0.125 mg to 2.0 mg.

3. The method of claim 1, wherein said subject is an animal.

* * * * *